(12) United States Patent
Cichutek et al.

(10) Patent No.: US 7,138,272 B1
(45) Date of Patent: Nov. 21, 2006

(54) GENE TRANSFER IN HUMAN LYMPHOCYTES USING RETROVIRAL SCFV CELL TARGETING

(75) Inventors: Klaus Cichutek, Langen (DE); Martin Engelstaedter, Roedermark (DE)

(73) Assignee: Bundesrepublik Deutschland, Langen (DE)

( * ) Notice: Subject to any disclaimer, the term of this patent is extended or adjusted under 35 U.S.C. 154(b) by 411 days.

(21) Appl. No.: 10/089,278

(22) PCT Filed: Jan. 17, 2002

(86) PCT No.: PCT/AU02/00048

§ 371 (c)(1),
(2), (4) Date: Oct. 29, 2003

(87) PCT Pub. No.: WO01/25415

PCT Pub. Date: Apr. 12, 2001

(30) Foreign Application Priority Data

Sep. 27, 1999 (DE) ................................ 199 46 142

(51) Int. Cl.
*C12N 15/00* (2006.01)
*C12N 15/63* (2006.01)

(52) U.S. Cl. ..................................... 435/320.1; 514/44
(58) Field of Classification Search ............. 435/320.1; 514/44
See application file for complete search history.

(56) References Cited

FOREIGN PATENT DOCUMENTS

| CA | 2311602 A1 | 6/1999 |
|---|---|---|
| DE | 197 52 854 A1 | 7/1999 |
| WO | WO 96/36360 | 11/1996 |
| WO | WO 98/51787 | 11/1998 |

OTHER PUBLICATIONS

Verma et al. Gene therapy-promises, problems and prospects, Nature, 1997, vol. 389, pp. 239-242.*
Marshall, E. Gene therapy's growing pains. Science, 1995, vol. 269, p. 1050-1055.*
Juengst, E.T. What next for human gene therapy? British Medical Journal, 2003, vol. 3326, pp. 1410-1411.*
Rubanyi, G.M. The future of gene therapy. Molecularr Aspects of Medicine, 2001, vol. 22, pp. 113-142.*
Eck et al. Goodman and Gilman's The pharmacological basis of therapeutics, 1996, McGraw-Hill, NY, 9th Edition, Chapter 5, pp. 77-100.*
Ross et. Gene therapy in the United States: A five-year staus report. Human Gene therapy, 1996, vol. 7, pp. 1781-1790.*
Marusich et al. Spleen necrosis virus-based vector delivery of anti-HIV-1 genes potently protects cells from HIV-1 infection. Virology (2005, vol. 332, pp. 258-271.*
Galanis et al. Delivery systems intended for in vivo gene therapy of cancer: targeting and replication competent viral vectors. Crtical Reviews in Oncology and Hematology (2001) vol. 38, pp. 177-192.*
Karavanas et al. Cell targeting by murine retroviral vectors. Crtical Reviews in Oncology and Hematology (1998) vol. 28, pp. 7-30.*
Anderson, "Human Gene Therapy", *Science*, vol. 256:808-813 (1992).
Chang et al., "Block of HIV-1 infection by a combination of antisense tat RNA and TAR decoys: a strategy for control of HIV-1", *Gene Therapy*, vol. 1:208-216 (1994).
Chu et al., "Toward Highly Efficient Cell-Type-Specific Gene Transfer with Retroviral Vectors Displaying Single-Chain Antibodies", *J. Virol.*, vol. 71:720-725 (1997).
Chu et al., "Cell targeting with retroviral vector particles containing antibody-envelope fusion proteins", *Gene Therapy*, vol. 1:292-299 (1994).
Cosset et al., "Retroviral Retargeting by Envelopes Expressing an N-Terminal Binding Domain", *J. Virol.*, vol. 69:6314-6322 (1995).
Duan et al., "Intracellular Immunization Against HIV-1 Infection of Human T Lymphocytes: Utility of Anti-Rev Single-Chain Variable Fragments", *Human Gene Therapy*, vol. 6:1561-1573 (1995).
Dornburg, "Reticuloendotheliosis viruses and derived vectors", *Gene Therapy*, vol. 2:301-310 (1995).
Engelstadter et al., "Targeting Human T Cells by Retroviral Vectors Displaying Antibody Domains Selected from a Phage Display Library", *Human Gene Therapy*, vol. 11:293-303 (2000).
Huston et al., "Protein Engineering of Single-Chain Fv Analogs and Fusion Proteins", *Methods in Enzymology*, vol. 203:46-88 (1991).
Jiang et al., "Cell-Type-Specific Gene Transfer into Human Cells with Retroviral Vectors That Display Single-Chain Antibodies", *J. Virol.*, vol. 72:10148-10156 (1998).
Kasahara et al., "Tissue-Specific Targeting of Retroviral Vectors Through Ligand-Receptor Interactions", *Science*, vol. 266:1373-1375 (1994).
Leavitt et al., "Ex vivo transduction and expansion of CD4+ lymphocytes from HIV+ donors: prelude to a ribozyme gene therapy trial", *Gene Therapy*, vol. 3:599-606 (1996).
Levy-Mintz et al., "Intracellular Expression of Single-Chain Variable Fragments To Inhibit Early Stages of the Viral Life Cycle by Targeting Human Immunodeficiency Virus Type 1 Integrase", *J. Virol.*, vol. 70:8821-8832 (1996).
Macchi et al., "Mutations of Jak-3 gene in patients with autosomal severe combined immune deficiency (SCID)", *Nature* vol. 377:65-68 (1995).
Martinez et al., "Improved Retroviral Packaging Lines Derived from Spleen Necrosis Virus", *Virology*, vol. 208:234-241 (1995).
Martinez et al., "Mapping of Receptor Binding Domains in the Envelope Protein of Spleen Necrosis Virus", *J. Virol.* vol. 69:4339-4346 (1995).

(Continued)

*Primary Examiner*—Celine Qian
*Assistant Examiner*—Tara L. Garvey
(74) *Attorney, Agent, or Firm*—Fish & Richardson P.C.

(57) ABSTRACT

The invention relates to gene transfer into human T cells using novel retroviral scFv cell targeting vectors and using these vectors for the treatment of T-cell-associated diseases.

4 Claims, 5 Drawing Sheets

OTHER PUBLICATIONS

Mikawa et al., "*In Vivo* Analysis of a New lacZ Retrovirus Vector Suitable for Cell Lineage Marking in Avian and Other Species", *Exp. Cell Res.*, vol. 195:516-523 (1991).

Morgan et al., "Analysis of the Functional and Host Range-Determining Regions of the Murine Exotropic and Amphotropic Retrovirus Envelope Proteins", *J. of Virol.*, vol. 67:4712-4721 (1993).

Ramenzani et al., "Inhibition of HIV-1 replication by retroviral vectors expressing monomeric and multimeric hammerhead ribozymes", *Gene Therapy*, vol. 4:861-867 (1997).

Russell et al., "Retroviral vectors displaying functional antibody fragments", *Nucleic Acids Res.*, vol. 21:1081-1085 (1993).

Schnierle et al., "Pseudotyping of murine leukemia virus with the envelope glycoproteins of HIV generates a retroviral vector with specificity of infection for CD4-expressing cells", *Proc. Natl. Acad. Sci. USA*, vol. 94:8640-8645 (1997).

Smith et al., "Transient protection of human T-cells from human immunodeficiency virus type 1 infection by transduction with adeno-associated viral vectors which express RNA decoys", *Antiviral Research*, vol. 32:99-115 (1996).

Watanabe et al., "Construction of a Helper Cell Line for Avian Reticuloendotheliosis Virus Cloning Vectors", *Mol. Cell Biol.*, vol. 3:2241-2249 (1983).

Weiss, "Cellular Receptors and Viral Glycoproteins Involved in Retrovirus Entry", *The Retroviridae* vol. 2:1-108 (1993).

Whitlow et al., "Single-Chain Fv Proteins and Their Fusion Proteins", *Methods: A Companion to Methods Enzymol.*, vol. 2:97-105 (1991).

Yu et al., "Gene Therapy for Metastatic Brain Tumors by Vaccination with Granulocyte-Macrophage Colony-Stimulating Factor-Transduced Tumor Cells", *Human Gene Therapy*, vol. 8:1065-1072 (1997).

* cited by examiner

7A5-scFv

```
                                                    ► SNV-env Leader
  1 TCCACCACTCTCGACTCAAGAAAGCTCCTGACAACCAAGAAGA ATG GAC TGT CTC ACC AAC CTC CGA TCC  70
  1                                               M   D   C   L   T   N   L   R   S    9

71 GCT GAG GGT AAA GTT GAC CAG GCG AGC AAA ATC CTA ATT CTC CTT GTG GCT TGG TGG GGG  130
 10  A   E   G   K   V   D   Q   A   S   K   I   L   I   L   L   V   A   W   W   G    29
                                                      Sfi I       ► 7A5-scFv
131 TTT GGG ACC ACT GCC GAA GTT TCG ACT GCC CGA GCG GCC CAG CCG GCC ATG GCC GAG GTC  190
 30  F   G   T   T   A   E   V   S   T   A   R   A   A   Q   P   A   M   A   E   V    49

191 AAG CTG CAG CAG TCA GGG GCT GAG CTG GTG AGG CCT GGG GTC TCA GTG AAG ATT TCC TGC  250
 50  K   L   Q   Q   S   G   A   E   L   V   R   P   G   V   S   V   K   I   S   C    69

251 AAG GGT TCT GGC TAC ACA TTC ACT GAT TAT GGT ATG AGC TGG GTG AAA CAG AGT CAT GCA  310
 70  K   G   S   G   Y   T   F   T   D   Y   G   M   S   W   V   K   Q   S   H   A    89

311 AAG AGT CTA GAG TGG ATT GGA CTT ATT AGT ACT TAC TAT GGT GAT CCT AGT TAC AAC CAG  370
 90  K   S   L   E   W   I   G   L   I   S   T   Y   Y   G   D   P   S   Y   N   Q    109

371 AGG TTC AAG GGC AAG GCC ACA ATG ACT GTA GAC AAA TCC TCC AAC ACA GCC TAT TTG GAA  430
110  R   F   K   G   K   A   T   M   T   V   D   K   S   S   N   T   A   Y   L   E    129

431 CTT GCC AGA CTG ACA TCT GAG GAT TCT GCC ATT TAT TAT TGT GCA AGA TCG GAT GGT AAT  490
130  L   A   R   L   T   S   E   D   S   A   I   Y   Y   C   A   R   S   D   G   N    149

491 TAC GGG TAT TAC TAT GCT TTG GAC TAC TGG GGC CAA GGC ACT ACG GTC ACC GTC TCC TCA  550
150  Y   G   Y   Y   Y   A   L   D   Y   W   G   Q   G   T   T   V   T   V   S   S    169

551 GGT GGA GGC GGT TCA GGC GGA GGT GGC TCT GGC GGT GGC GGA TCG GAT ATC GAG CTC ACT  610
170  G   G   G   G   S   G   G   G   G   S   G   G   G   G   S   D   I   E   L   T    189

611 CAG TCT CCA TCT TCT TTG GCT GTG TCT CTA GGG CAG AGG GCC ACC ATA TCC TGC AGA GCC  670
190  Q   S   P   S   S   L   A   V   S   L   G   Q   R   A   T   I   S   C   R   A    209

671 AGT GAA AGT GTT GAT AGT TAT GGC GAT AGT TTT ATG CAC TGG TAT CAG CAG AAA CCA GGA  730
210  S   E   S   V   D   S   Y   G   D   S   F   M   H   W   Y   Q   Q   K   P   G    229

731 CAG CCA CCC AAA CTC CTC ATC TAT CGT GCA TCC AAC CTA GAA TCT GGA GTC CCT GCC AGG  790
230  Q   P   P   K   L   L   I   Y   R   A   S   N   L   E   S   G   V   P   A   R    249

791 TTC AGT GGC AGT GGG TCT GAG TCA GAC TTC ACT CTC ACC ATC GAT CCT GTG GAG GAA GAT  850
250  F   S   G   S   G   S   E   S   D   F   T   L   T   I   D   P   V   E   E   D    269

851 GAT GCT GCA GTG TAT TAC TGT CTG CAA AGT ATG GAA GAT CCG TAC ACG TTC GGA GGG GGG  910
270  D   A   A   V   Y   Y   C   L   Q   S   M   E   D   P   Y   T   F   G   G   G    289
                                           Not I
911 ACC AAG CTG GAA ATA AAA CGG GCG GCC GCA TCG GGC TCC GGG GGC GGT GGT TCT GGT GGT  970
290  T   K   L   E   I   K   R   A   A   A   S   G   S   G   G   G   G   S   G   G    309

971 GGT TCT GGT GGT GGT GGT TCT GGT GGT GGT GGT TCT GGC GCC AGC CCA GTC CAG TTT ATC 1030
310  G   S   G   G   G   G   S   G   G   G   G   S   G   A   S   P   V   Q   F   I    329
```

(SEQ ID NO: 1)
(SEQ ID NO: 6)

FIG. 1

K6-scFv

```
                                                          ▶ SNV-env Leader
   1                                               ATG GAC TGT CTC ACC AAC CTC CGA TCC   27
   1                                                M   D   C   L   T   N   L   R   S    9

28 GCT GAG GGT AAA GTT GAC CAG GCG AGC AAA ATC CTA ATT CTC CTT GTG GCT TGG TGG GGG     87
  10  A   E   G   K   V   D   Q   A   S   K   I   L   I   L   L   V   A   W   W   G     29
                                                            Sfi I      ▶ K6-scFv
  88 TTT GGG ACC ACT GCC GAA GTT TCG ACT GCC CGA GCG GCC CAG CCG GCC ATG GCC GAG GTC    147
  30  F   G   T   T   A   E   V   S   T   A   R   A   A   Q   P   A   M   A   E   V    49

148 AAG CTG CAG GAG TCA GGG ACT GAA CTT GTG AAG CCT GGG GCT TCA GTG AAT CTG TCT TGC    207
  50  K   L   Q   E   S   G   T   E   L   V   K   P   G   A   S   V   N   L   S   C    69

208 AAG GCT TCT GGC TAC ACC TTC ACC AGC TAC TGG ATG CAC TGG TTG AAG CAG AGG CCT GGA    267
  70  K   A   S   G   Y   T   F   T   S   Y   W   M   H   W   L   K   Q   R   P   G    89

268 CAA GGC CTT GAG TGG ATC GGA GAG ATT GAT CCT GTT GAT AGT TAT ACT AAC TAC AAT CAA    327
  90  Q   G   L   E   W   I   G   E   I   D   P   V   D   S   Y   T   N   Y   N   Q   109

328 AAC TTC AAG GGC AAG GCC ACA CTG ACT GTA GAC AAG TCC TCC ACC ACA GTC TAC ATG CAC    387
 110  N   F   K   G   K   A   T   L   T   V   D   K   S   S   T   T   V   Y   M   H   129

388 CTC AGC AGC CTG ACA TCT GAG GAC TCT GCG GTC TAT TAC TGT GCA AGA AAG GGC TAT GCT    447
 130  L   S   S   L   T   S   E   D   S   A   V   Y   Y   C   A   R   K   G   Y   A   149

448 ATG GAC TAC TGG GGC CAA GGG ACC AAC GTC ACC GTC TCC TCA GGT GGA TGC GGT TCA GGC    507
 150  M   D   Y   W   G   Q   G   T   N   V   T   V   S   S   G   G   C   G   S   G   169

508 GGA GGT GGC TCT GGC GGT GGC GGA TCG GAC ATC GAG CTC ACT CAG TCA CCA GCA ATC ATG    567
 170  G   G   G   S   G   G   G   G   S   D   I   E   L   T   Q   S   P   A   I   M   189

568 TCT GCA TCT CCA GGG GAG AAG GTC ACC ATG ACC TGC AGT GCC AGC TCA AGT ATA AGT TAC    627
 190  S   A   S   P   G   E   K   V   T   M   T   C   S   A   S   S   S   I   S   Y   209

628 ATG CAC TGG TAC CAG CAG AAG CCA GGC ACC TCC CCC AAA AGA TGG ATT TAT GAC ACA TCC    687
 210  M   H   W   Y   Q   Q   K   P   G   T   S   P   K   R   W   I   Y   D   T   S   229

688 AAA CTG GCT TCT GGA GTC CCT GCT CGC TTC AGT GGC AGT GGG TCT GGG ACC TCT TAT TCT    747
 230  K   L   A   S   G   V   P   A   R   F   S   G   S   G   S   G   T   S   Y   S   249

748 CTC CCA ATC AGC AGC ATG GAG GCT GAA GAT GCT GCC ACT TAT TAC TGC CAT CAG CGG AGT    807
 250  L   P   I   S   S   M   E   A   E   D   A   A   T   Y   Y   C   H   Q   R   S   269
                                                                              Not I
 808 AGT TAC CCA TGG ACG TTC GGT GGA GGG ACC AAG CTG GAA ATA AAA CGG GCG GCC GCA TCG    867
 270  S   Y   P   W   T   F   G   G   G   T   K   L   E   I   K   R   A   A   A   S   289

868 GGC TCC GGG GGC GGT GGT TCT GGT GGT GGT TCT GGT GGT GGT GGT TCT GGT GGT GGT GGT    927
 290  G   S   G   G   G   G   S   G   G   G   S   G   G   G   S   G   G   G   G   309
```

FIG. 2

(SEQ ID NO: 2)
(SEQ ID NO: 7)

-scFv

▸ SNV-env Leader

```
     TG GAC TGT CTC ACC AAC CTC CGA TCC GCT GAG GGT AAA GTT GAC CAG GCG AGC AAA ATC   60
         D   C   L   T   N   L   R   S   A   E   G   K   V   D   Q   A   S   K   I   20

TA ATT CTC CTT GTG GCT TGG TGG GGG TTT GGG ACC ACT GCC GAA GTT TCG ACT GCC CGA  120
         I   L   L   V   A   W   W   G   F   G   T   T   A   E   V   S   T   A   R   40
                       Sfi I      ▸ 7B2-scFv
     CG GCC CAG CCG GCC ATG GCC CAG GTG CAG CTG CAG CAG TCT GGG ACT GAA CTG GCA ACA  180
         A   Q   P   A   M   A   Q   V   Q   L   Q   Q   S   G   T   E   L   A   T   60

CT GGG GCC TCA GTG AGG ATG TCC TGC AAG GCT TCT GGC TAC GCC TTT ACT ACC TAC TGG  240
         G   A   S   V   R   M   S   C   K   A   S   G   Y   A   F   T   T   Y   W   80

TG CAC TGG GTA AAA CAG AGG CCT GGA CAG GGT CTG GAA TGG ATT GGA TAC ATT AAT CCT  300
         H   W   V   K   Q   R   P   G   Q   G   L   E   W   I   G   Y   I   N   P  100

301  ACC ACT GAT TAT ACT GAC TAC AAT CTG AAG TTC AAG GAC AAG GCC ACA TTG ACT GCA GAC  360
101   T   T   D   Y   T   D   Y   N   L   K   F   K   D   K   A   T   L   T   A   D  120

361  AAA TCC TCC AGT ACA GCC TAC ATG CAA CTG AGC AGC CTG ACA TCT GAG GAC TCT GCA GTC  420
121   K   S   S   S   T   A   Y   M   Q   L   S   S   L   T   S   E   D   S   A   V  140

421  TAT TAC TGT GCA AGA TCG GGG TGG TCC TAT GCT ATG GAC TAC TGG GGG CAA GGG ACC ACG  480
141   Y   Y   C   A   R   S   G   W   S   Y   A   M   D   Y   W   G   Q   G   T   T  160

481  GTC ACC ATC TCC TCA GGT GGA GGC GGT TCA GGC GGA GGT GGC TCT GGC GGT GGC GGA TCG  540
161   V   T   I   S   S   G   G   G   G   S   G   G   G   G   S   G   G   G   G   S  180

541  GAC ATC GAG CTC ACT CAG TCT CCA GCA ATC ATG TCT GCA TCT CCA GGG GAG AAG GTC ACC  600
181   D   I   E   L   T   Q   S   P   A   I   M   S   A   S   P   G   E   K   V   T  200

601  ATA ACC TGC AGT GCC AGC TCA AGT GTA AGT TAC ATG CAC TGG TTC CAG CAG AAG CCA GGC  660
201   I   T   C   S   A   S   S   S   V   S   Y   M   H   W   F   Q   Q   K   P   G  220

661  ACT TCT CCC AAA CTC TGG ATT TAT AGC ACA TCC AAC CTG GCT TCT GGA GTC CCT GCT CGC  720
221   T   S   P   K   L   W   I   Y   S   T   S   N   L   A   S   G   V   P   A   R  240

721  TTC AGT GGC AGT GGA TCT GGG ACC TCT TAC TCT CTC ACA ATC AGC CGA ATG GAG GCT GAA  780
241   F   S   G   S   G   S   G   T   S   Y   S   L   T   I   S   R   M   E   A   E  260

781  GAT GCT GCC ACT TAT TAC TGC CAG CAA AGG AGT AGT TAC CCA TTC ACG TTC GGC TCG GGC  840
261   D   A   A   T   Y   Y   C   Q   Q   R   S   S   Y   P   F   T   F   G   S   G  280
                                                  Not I
841  ACC AAG CTG GAA ATC AAA CGG GCG GCC GCA TCG GGC TCC GGG GGC GGT GGT TCT GGT GGT  900
281   T   K   L   E   I   K   R   A   A   A   S   G   S   G   G   G   G   S   G   G  300

901  GGT GGT TCT GGT GGT GGT GGT TCT GGT GGT GGT GGT TCT GGC GCC AGC CCA GTC CAG TTT  960
301   G   G   S   G   G   G   G   S   G   G   G   G   S   G   A   S   P   V   Q   F  320

961  ATC CCC CTG CTT GTG GGT CTA GGG ATT TCA                                          990
321   I   P   L   L   V   G   L   G   I   S                                          330
```

FIG. 3

(SEQ ID NO: 3)
(SEQ ID NO: 8)

7E4-scFv

▶ SNV-env Leader

```
  1 ATG GAC TGT CTC ACC AAC CTC CGA TCC GCT GAG GGT AAA GTT GAC CAG GCG AGC AAA ATC  60
  1  M   D   C   L   T   N   L   R   S   A   E   G   K   V   D   Q   A   S   K   I   20

61 CTA ATT CTC CTT GTG GCT TGG TGG GGG TTT GGG ACC ACT GCC GAA GTT TCG ACT GCC CGA 120
 21  L   I   L   L   V   A   W   W   G   F   G   T   T   A   E   V   S   T   A   R   40
             Sfi I        ▶ 7E4-scFv
121 GCG GCC CAG CCG GCC ATG GCC GAG GTC AAG CTG CAG CAG TCA GGG GCT GAG CTG GTG AGG 180
 41  A   A   Q   P   A   M   A   E   V   K   L   Q   Q   S   G   A   E   L   V   R   60

181 CCT GGA GCT TCA GTG AAG CTG TCC TGC AAG ACT TCT GGC TTC TCC TTC ACC AGC TAC TGG 240
 61  P   G   A   S   V   K   L   S   C   K   T   S   G   F   S   F   T   S   Y   W   80

241 ATG AAC TGG GTG AAG CTG AGG CCT GGA CAA GGC CTT GAG TGG ATT GGC ATG ATT CAT CCT 300
 81  M   N   W   V   K   L   R   P   G   Q   G   L   E   W   I   G   M   I   H   P  100

301 TCC GAT AGT GAA ACT AGT TTA ACT CAG AGG TTC AAG GAC AAG GCC ACA CTG ACT GTA GAC 360
101  S   D   S   E   T   S   L   T   Q   R   F   K   D   K   A   T   L   T   V   D  120

361 AAA TCC TCC AGC ACA GCC TAC ATG CAA CTC AGC AGC CCG ACA TCT GAG GAC TCT GCG GTC 420
121  K   S   S   S   T   A   Y   M   Q   L   S   S   P   T   S   E   D   S   A   V  140

421 TAT TAC TGT GCA AGA TCT CTT TAT GCT AAC TAC CCC TCC TGG TTT ACT TAC TGG GGC CAA 480
141  Y   Y   C   A   R   S   L   Y   A   N   Y   P   S   W   F   T   Y   W   G   Q  160

481 GGC ACC ACG GTC ACC GTC TCC TCA GGT GGA GGC GGT TCA GGC GGA GGT GGC TCT GGC GGT 540
161  G   T   T   V   T   V   S   S   G   G   G   G   S   G   G   G   S   G   G  180

541 GGC GGA TCG GAC ATC GAG CTC ACT CAG TCT CCA ACC ACC ATG GCT GCA TCT CCC GGG GAG 600
181  G   G   S   D   I   E   L   T   Q   S   P   T   T   M   A   A   S   P   G   E  200

601 AAG ATC ACT ATC ACC TGC AGT GCC AGC TCA AGT ATA AGT TCC AAT TAC TTG CAT TGG TAT 660
201  K   I   T   I   T   C   S   A   S   S   S   I   S   S   N   Y   L   H   W   Y  220

661 CAG CAG AAG CCA GGA TTC TCC CCT AAA CTC TTG ATT TAT AGG ACA TCC AAT CTG GCT TCT 720
221  Q   Q   K   P   G   F   S   P   K   L   L   I   Y   R   T   S   N   L   A   S  240

721 GGA GTC CCA GCT CGC TTC AGT GGC AGT GGG TCT GGG ACC TCT TAC TCT CTC ACA ATT GGC 780
241  G   V   P   A   R   F   S   G   S   G   S   G   T   S   Y   S   L   T   I   G  260

781 ACC ATG GAG GCT GAA GAT GTT GCC ACT TAC TAC TGC CAG CAG GGT AGT AGT ATA CCG TAC 840
261  T   M   E   A   E   D   V   A   T   Y   Y   C   Q   Q   G   S   S   I   P   Y  280
                                                                   Not I
841 ACG TTC GGA GGG GGG ACC AAG CTG GAA ATA AAA CGG GCG GCC GCA TCG GGC TCC GGG GGC 900
281  T   F   G   G   G   T   K   L   E   I   K   R   A   A   A   S   G   S   G  300

901 GGT GGT TCT GGT GGT GGT GGT TCT GGT GGT GGT GGT TCT GGT GGT G                    946
301  G   G   S   G   G   G   G   S   G   G   G   G   S   G   G                      315
```

FIG. 4

(SEQ ID NO: 4)
(SEQ ID NO: 9)

6C3-scFv

▶ SNV-env Leader

```
  1 ATG GAC TGT CTC ACC AAC CTC C

# GENE TRANSFER IN HUMAN LYMPHOCYTES USING RETROVIRAL SCFV CELL TARGETING

CROSS-REFERENCE TO RELATED APPLICATION

This application is the National Stage of International Application No. PCT/DE00/03444 filed on Sep. 27, 2000, which claims priority from German Patent Application No. 199 46 1422, filed on Sep. 27, 1999, both of which are incorporated herein by reference in their entirety.

FIELD OF THE INVENTION

Background of the Invention

The invention relates to the gene transfer into human lymphocytes, in particular T-lymphocytes using retroviral scFv cell targeting vectors and the use of said vectors for gene therapy, vaccination therapy or diagnostics, in particular for the therapy of T-cell-associated diseases.

The majority of retroviral vectors currently used in gene therapeutic research are derived from the amphotropic murine leukemia virus (MLV). The host cell range of the amphotropic MLV is determined by the surface envelope protein (SU) encoded by the env gene. The protein products of the env gene form the outer envelope of the retroviral vector. The SU proteins interact with i.e. bind to a particular protein (receptor) on the surface of the host cell. The env gene products of the amphotropic MLV allow the gene transfer in a large number of different mammal cells. However, a selective gene transfer into specific cell or tissue types of human or other mammals is not possible with amphotropic MLV vectors since the receptor for the MLV envelope protein on the surface of mammal cells which mediates the entry of amphotropic MLV vectors and the gene transfer may be found on nearly all these cells. Thus, the host cell range of the amphotropic MLV is not specific.

A host cell specificity e.g. is advantageous for the gene therapeutic use, since in a gene therapy outside of the organism (ex vivo) (Anderson et al., 1992; Yu et al., 1997) extensive purifications of the cells are avoided. For the therapeutic, diagnostic or vaccination use in vivo it is desired that retroviral vectors specifically target the desired host cells prior to the transfer of the therapeutic gene. A restriction of the host cell range of the amphotropic MLV could be achieved by modification of the surface envelope protein. A modification of the surface envelope protein was carried out by fusion with a hormone domain. The cells bearing the hormone receptor were transduced (Kasahara et al., 1995). Furthermore, the surface envelope protein has been modified by fusion with a single chain antibody fragment (single chain variable fragments, in the following also referred to as "scFv"). The fragment represented the antigen binding domain of an antibody and is a fusion protein composed of the variable domain Vh and Vl of a monoclonal antibody. The two domains are bound via a glycine and serine oligopeptid [(-(ser-gly4)3-gly-)] enabling the correct folding of the fusion protein (Huston et al, 1991; Whitlow et al., 1991). All modifications carried out heretofore of the MLV surface envelope protein with a scFv show that although the vectors bound to the host target cell no entry into the cell occurred (Russel et al., 1993). Furthermore, it is known that the surface envelope protein of the MLV generally enables no extensive modifications (Cosset et al., 1995). Modifications in which a part of the binding domain of the MLV-SU protein has been replaced often led to an incorrect processing and thus to a defective transport of the SU protein to the cell surface (Weiss et al., 1993; Morgan et al., 1993; Russel et al., 1993). Thus, the development of cell specific retroviral vectors on the base of MLV having altered surface envelope proteins is only less promising.

Retroviral vectors on the base of Spleen Necrosis Virus SNV are more suitable for a targeted gene transfer into e.g. human cells since the surface envelope protein of SNV enables extensive modifications and is also correctly processed (Martinez and Dornburg 1995; Chu and Dornburg, 1994, 1995; Jiang et al., 1998). For the preparation of such vectors at least two components are required. To the one hand, a so-called expression construct has to be prepared which enables a packaging into and the transfer through a retrovirus. The expression construct comprises a coding DNA fragment of the desired gene product, e.g. a gene for gene therapy or as a vaccine. The expression construct has to comprise a nucleotide sequence referred to as packaging signal psi (ψ) which directs the efficient packaging of the mRNA into retroviral particles. Further, a packaging or helper cell is required which provides the gag, pol and env gene products of SNV without packaging the gag, pol and env genes into a retrovirus. The gag, pol and env genes present in the packaging cell have to be psi-negative. After transfer of the expression construct by transfection of the corresponding plasmide DNA into the packaging cells retroviral particles are delivered into the cell culture supernatant, said particles containing the expression construct and being able to transfer only this gene but not the gag, pol and env genes into the target cell. These vectors are unable to propagate and run only through one replication round. The general process for the preparation of propagation unable retroviral vectors is state of the art (Russel et al., 1993, Cosset et al., 1995; Weiss et al., 1993; Morgan et al., 1993; Martinez and Dornburg, 1995; Chu and Dornburg, 1994, 1995; Jiang et al., 1998).

Also the tropism (host cell specificity of the Spleen Necrosis Virus) is determined by the surface envelope protein (SU protein) encoded by the SNV env gene. The SNV surface envelope wild type protein does not permit any selective gene transfer into particular cells or tissues of humans, since the specific recipient protein (receptor) is not present on the surface of human cells (Dornburg, 1995). Therefore, a process has been developed by Dornburg et al., to replace the SNV SU protein for the antigen recognizing domains of antibodies. Said [SNV scFV Env] vectors with four different scFv known heretofore were able to transfer the psi-positive reporter gene, i.e. the bacterial β galactosidase, into selected human target cells (Chu et al., 1994; Chu et al., 1995; Chu and Dornburg, 1997). In detail, there are two scFv expressed against unknown surface antigens on breast and colon carcinoma cells (Chu et al., 1995; Chu and Dornburg, 1997; Jiang et al., 1998), i.e. an scFv directed against the human transferrine receptor and an scFv which recognizes the CD34 surface antigen. A packaging cell line (DSH CXL) has been developed, containing both the psi-negative SNV genes gag, pol and env and the psi-positive reporter-gene (pCXL). Following transfection of the packaging cell with the plasmide DNA of a further expression gene (pTC 53 [expression vector pTC53 and pTC53zeo Jiang et al., 1998]), in which the entire surface envelope protein has been replaced against a single chain antibody fragment (scFv), retroviral vectors were delivered into the cell supernatant which bore in addition to the surface envelope wild-type protein also the chimeric [scFv-Env] surface protein on their surface. By means of said vectors the reporter gene could be transferred into the scFv-specific target cells. In the process described by Dornburg et al., for the preparation of cell specific retroviral vectors it is true that only already known and cloned scFv may be used.

SUMMARY OF THE INVENTION

DE 19752854 A1 describes a method for the preparation of cell type-specific targeting vectors derived from SNV. Up to now, 4 scFv-SNV targeting vectors have been described. They are directed against tumor markers, the transferrine receptor and the CD34 surface antigen (Chu & Dornburg, 1995, 1997, Jiang et al., 1997). Here, the scFv have been derived from monoclonal antibodies (mAb). Furthermore, pseudotype vectors of the type MLV (HIV) for specific transduction of human CD4-positive T cells have been described already (Schnierle & Stitz et al., 1997).

However, no vectors have been described up to now, which are able to transduce human T-cells in a CD4-independent manner.

Thus, an object of the present invention was to provide T-cell specific vectors which are able to transduce T cells in a CD4-independent manner.

The object is solved by cell targeting vectors containing a DNA sequence encoding a single chain antibody fragment (single chain variable fragment, scFv), wherein the single chain antibody fragment has an amino-acid sequence according to any of the FIGS. 1 to 5.

In a preferred embodiment the cell targeting vector further contains a DNA sequence encoding a SNV-env leader according to any of the FIGS. 1 to 5. The cell targeting vectors according to the present invention are T-cell-specific, i.e. the vectors selectively induce human T cells in a CD4 independent manner.

In a further preferred embodiment, the cell targeting vector is derived from SNV (Spleen Necrosis Virus), particularly preferred is the vector pTC53 derived from SNV.

In a further embodiment of the present invention the cell targeting vectors of the invention contain a therapeutic gene. Thus, the invention also relates to the use of the cell targeting vectors of the invention for gene therapy, vaccination therapy or diagnostics.

BRIEF DESCRIPTION OF THE DRAWINGS

FIG. 1 is a representation of a nucleic acid sequence of the invention, 7A5-scFv (SEQ ID NO:1), and the amino acid sequence it encodes (SEQ ID NO:6).

FIG. 2 is a representation of a nucleic acid sequence of the invention, K6-scFv (SEQ ID NO:2), and the amino acid sequence it encodes (SEQ ID NO:7).

FIG. 3 is a representation of a nucleic acid sequence of the invention, 7B2-scFv (SEQ ID NO:3), and the amino acid sequence it encodes (SEQ ID NO:8).

FIG. 4 is a representation of a nucleic acid sequence of the invention, 7E4-scFv (SEQ ID NO:4), and the amino acid sequence it encodes (SEQ ID NO:9).

FIG. 5 is a representation of a nucleic acid sequence of the invention, 6C3-scFv (SEQ ID NO:5), and the amino acid sequence it encodes (SEQ ID NO:10).

DETAILED DESCRIPTION

By having the scFv vectors of the invention the first scFv cell targeting vectors are available which are able to transduce human T cells in a CD4-independent manner with a differently high efficiency.

By means of the vectors of the invention, it is now possible to treat following T-cell associated diseases.

(i) Severe Combined Immunodeficiency (SCID). This is a defect in the adenosine-desaminase gene (ada) or the gene encoding thyrosin kinase JAK-3 (Macchi et al., 1995). As a therapeutic Gene the intact ada gene is transferred into T cells by means of the vectors of the present invention.

(ii) Acquired Immunodeficiency Syndrome (AIDS) is caused by HIV-1 infection. Therapeutic genes should inhibit the replication or integration of the virus. As therapeutic gene products for intracellular immunization ribozymes, decoy RNA, transdominantly negative mutants of HIV proteins or antibody fragments are suitable (Chang et al., 1994, Ramenzani et al., 1997, Smith et al., 1996, Leavitt et al., 1996, Duan et al., 1995, Levy-Mintz et al., 1996). These therapeutic genes are transferred into the T cells of HIV-1-infected patients by the use according to the invention of the novel cell targeting vectors.

It has been shown that by means of the vectors of the invention (e.g. vectors containing scFv 7A5 shown in FIG. 1; in the following referred to as 7A5 vectors) human macrophages are transduced with a 95% efficiency. Thus, the transfer of therapeutic genes is also possible in HIV-1-infected macrophages by means of said 7A5 vectors.

(iii) T-cell-associated lymphomas.

The (scFv-SNV-Env) targeting vectors of the invention containing a DNA sequence encoding a single chain antibody fragment (single chain variable fragment, scFv), wherein the single chain antibody fragment has an amino-acid sequence (or a fragment) according to any of the FIGS. 1 to 5 selectively enable a transduction of human T-cell lines and partly of primary lymphocytes isolated from blood.

Surprisingly, the vectors of the invention show a selectivity for human T cells which is many times over that for other human cells. The 7-A5-vectors, i.e. the vectors encoding the single chain antibody fragment according to FIG. 1 or a portion thereof, showed a selectivity for human T cells which was increased by a factor of 1000 compared to that for other human cells (c.f. Table 2) and a 4–5 times increased selectivity for T cells compared to B cells.

Table 1 represents 5 scFv (in detail: 7A5, K6, 7B2, 7E4, 6C3) and their vector titers on human T cells (C8166), D17 cells (canine osteosarcoma cell line, permissive for SNV) and HeLa cells (human cervical carcinoma cell line).

Table 2 represents the vector titers of 7A5 vectors. From these data the efficiency and specificity for human T-cells are obvious. By means of said 7A5 vectors T cells which have been made quiescent by gene technologically modified SNV vectors and even human macrophages could be transduced in a very effective manner Thes following examples illustrate the invention and are not construed to be limiting:

Example 1

Determination of the Vector Titers of 5 Selected scFv on D17, C8166 and HeLa Cells.

For this purpose cell culture supernatants were titered in three serial dilutions (1000 µl, 100 µl and 10 µl) in a total volume of 1000 µl by adding 30 µg/ml polybren on the cells ($2\times10^5$ D17 and HeLa, $5\times10^5$ C8166). After a 1,5-2 h incubation period the vector containing supernatant was replaced by fresh medium.

Following 48 h an X-gal staining was used to detect transduced cells (Mikawa et al., 1992), and the blue cells were counted. Tab. 1 shows the vector titers of the 5 selected scFv on D17, C8166 and HeLa cells.

The titration on D17 (canine osteosarcoma cell line, Watanabe et al, 1983) functions as a positive control for the vector production. The titre of $>10^6$ i.U./ml shows that all 5 scFv packaging cell clones deliver vector particles into the cell culture supernatant with about the same efficiency.

The titer on C8166 cells vary between $10^3$ and $10^6$ i.U./ml depending on scFv, while the transduction on HeLa cells revealed no appreciable titer. Said fact indicates a high selectivity for human T cells of all 5 scFv vectors. The 7A5 vectors most efficiently transduce human T cells (Table 1).

TABLE 1

Vector titers of the 5 scFv vectors.

| ScFv | Titer (i.U./ml) | | |
|---|---|---|---|
| | D17 | C8166 | HeLa |
| 7A5 | $>10^6$ | $1 \times 10^6$ | $<10^2$ |
| K6 | $>10^6$ | $2.5 \times 10^5$ | $<10^1$ |
| 7B2 | $>10^6$ | $2 \times 10^4$ | $<10^1$ |
| 7E4 | $>10^6$ | $2 \times 10^3$ | $<10^1$ |
| 6C3 | $>10^6$ | $2 \times 10^3$ | $<10^1$ |

E=xample 2

Further Characterization of the Vectors

For a detailed characterization, further transduction experiments were carried out with the vectors. In Table 2, the results of the 7A5 vectors are represented.

TABLE 2

Transduction of different cell types by means of 7A5 and wild type vectors
Titer (i.U/ml)

| | D17 | HeLa | TE671 | HT1080 | 293T | C8166 | Molt4/8 | Jurkat | A301 | huPBMC |
|---|---|---|---|---|---|---|---|---|---|---|
| WT | $>10^6$ | $<10^1$ | $<10^1$ | $<10^1$ | $<10^1$ | $<10^1$ | $<10^1$ | $<10^1$ | $<10^1$ | $<10^1$ |
| 7A5 | $>10^6$ | $<10^2$ | $<10^1$ | $<10^1$ | $<10^2$ | $1 \times 10^5$ | $1 \times 10^6$ | $3 \times 10^5$ | $1 \times 10^5$ | $7.5 \times 10^4$ |

The transductions were carried out as described above. As a control, all cells were transdued with wild type vectors (WT). These are vector particles only containing the SNV Env wild type protein and no scFv. They are delivered from the starting packaging cell line DSH-cx1 (Chu & Dornburg, 1995, Jiang et al., 1998) into the culture supernatant. As expected, said vectors were not able to transduce human cells. Only the D17 cells which were permissive for them could be transduced with high efficiency.

The titration with 7A5 vectors showed an efficient transduction of several human T cell lines (C8166, Molt4-8, Jurkat, A301), while other human cell types (HeLa: cervical carcinoma, TE671: rhabdomyosarcoma, HT1080; fibrosarcoma, 293T; medulla renalis) could not be transduced. These results show that 7A5 vectors have a high selectivity for T cells.

An increased selectivity for T cells was also found for cell targeting vectors containing a DNA sequence encoding a single chain antibody fragment according to FIGS. 2, 3, 4 or 5.

Example 3

Transduction of Primary T Cells

For the transduction of primary T cells, primary human PBMC ("peripheral blood mononuclear cells", the isolation of PBMC from blood by means of sucrose density gradient centrifugation is carried out according to standard methods) were isolated from blood.

After a three days stimulation by means of PHA (phytohemagglutinin) and IL-2 the cell population consisted of 98% T lymphocytes (determined by FACS analysis with an antibody against T cell marker CD3 (state of the art).

The transduction of said cells by means of 7A5 vectors revealed an efficiency of 20% vector positive cells (or approx. $1\times10^5$ i.U./ml). As a comparison, the transduction experiments were carried out with human B cells. These could be transduced 5 times less (approx. 4%) than T cells.

Further, stimulated human PBMC could be transduced also with K6 and 7B2 vectors (i.e. vectors encoding the single chain antibody fragment according to FIG. 2 or 3 or a portion thereof). However, this occurred with an efficiency approx. 10 times less than with the 7A5 vectors.

LITERATURE

ANDERSON, (1992) Human Gene Therapy. Science 256: 808–813

CHANG H. K., GENDELMAN R, LISZIEWICZ J., GALLO R. C., ENSOLI B. (1994). Block of HIV-1 infection by a combination of antisense tat RNA and TAR decoys: a strategy for control of HIV-1. Gene Therapy 1: 208–216

CHU, T.-H. and DORNBURG, R (1995). Retroviral vector particles displaying the antigen-binding site of an antibody enable cell-type-specific gene transfer. J. Virol. 69, 2659–2663

CHU, T.-H. and DORNBURG, R. (1997). Toward highly efficient cell-type-specific gene-transfer with retroviral vectors displaying single-chain antibodies. J. Virol. 71, 720–725

CHU, T.-H.-T., MARTINEZ, I, SHEAY, W., DORNBURG R. (1994). Cell targeting with retroviral vector particles containing antibody-Envelope fusion proteins. Gene Therapy 1: 292–299

COSSET, F., MORLING, F., TAKEUCHI, Y., WEISS, R, COLLINS, M., RUSELL, S. (1995). Retroviral Retargeting by Envelopes Expressing an N-terminal Binding Domain. J. Virol 69, No. 10: 6314–632

DUAN L., ZHU M., BAGASRA O., POMERANTZ R. J. (1995). Intracellular immunization against HIV-1 infection of human T lymphocytes: utility of anti-Rev single-chain variable fragments. Hum. Gene Ther. 6: 1561–1573

DORNBURG, R (1995). Reticuloendeteliosis viruses and derived vectors. Gene Therapy 2: 1–10

ENGELSTÄDTER M, BOBKOVA, M., BAIER, M, STITZ, J., HOLTKAMP, N., CHU, T.- H.-T., KURTH, R., DORNBURG, R, BUCHHOLZ, C. J., AND CICHUTEK, K. Targeting human T-cells by retroviral vectors displaying antibody domains selected from a phage display library. (submitted to Human Gene Therapy)

HUSTON, J. S., MUDGETT-HUNTER, M., TAI, M. S., MCCARTHNEY, J., WARREN, F., HABER, E., (1991). Protein engineering of single-Chain Fv proteins and fusion proteins. Methods Enzymol. 203:46–88

JIANG A., CHU, T.-R, NOCKEN, F., CICHUTEK, K., and DORNBURG, R. (1998). Cell-type specific gene transfer into human cells with retroviral vectors that display single-chain antibodies. J. Virol. 72, 10148–10156

KASAHARA. N., DOZY, A. M., YUET WAI KAN (1994). Tissue-Specific Targeting of Retroviral Vectors Through Ligand-Receptor Interactions. Science 266: 1373–1375

LEAVITT M. C., WONG-STAAL F., LOONEY D. J. (1996). Ex vivo transduction and expansion of CD4+ lymphocytes from HIV+ donors: a prelude to a ribozyme gene therapy trial. Gene Ther. 7: 599–606

LEVY-MINTZ P., DUAN L., ZHANG H., HU B., DORNADULA G., ZHU M., KULKOSKI J., BIZUB-BENDER D., SKALKA A. M., POMERANZ R. J. (1996). Intracellular expression of single-chain variable fragments to inhibit early stages of the viral life cycle by targeting human immunodeficiency virus type 1 integrase. J. Virol. 70: 8821–8832

MACCHI P., VILLA A., GILIANI S., SACCO M. C., FRATTINI A, PORT F., UGAZIO A. G., JONSTON J. A, CANDOTTI F., O SHEA J. J., VEZZONI P., NOTARANGELO L. D. (1995). Mutations of the JAK-3 gene in patients with autosomal severe combined immune deficiency (SCID). Nature 377: 65–68

MARTINEZ, I. and DORNBURG, R (1995). Improved retroviral packaging cell lines derived from spleen necrosis virus. Virology 208, 234–241

MARTINEZ, I., DORNBURG, R. (1995). Mapping of Receptor Binding Domains in the Envelope Protein of Spleen Necrosis Virus. J. Virol. 69, No. 7

MIKAWA, T., FISCHMANN, D. A, DOUGHERTY, J. P., and BROWN, A. M. C. (1992). In vivo analysis of a new lacZ retrovirus vector suitable for lineage marking in avian and other species. Exp. Cell Res. 195, 516–523

MORGAN, R. A, NUSSBAUM, O., MUENCHAU, D. D.,-SHU, L., COUTRE, L., ANDESON, W. F. (1993). Analysis of the functional and the host range-determining regions of the murine ecotropic and amphotropic retrovirus envelope proteins. J. Virol. 67: 4712–4721

PARVEEN, Z., KRUPETZKI, A, POMERANTZ, R. J., ENGELSTÄDTER, M., CICHUTEK, K., AND DORNBURG, R. Genetically engineered c-type retroviral vectors, derived from spleen necrosis virus, SNV, capable of infecting quiescent cells. (submitted to Nature Biotechnology)

RAMENZANI A, DING S. F., JOSHI S. (1997). Inhibition of HIV-1 replication by retroviral vectors expressing monomeric and multimeric hammerhead ribozymes. Gene Ther. 4: 861–867

RUSSEL, S, J., HAWKINS, R. E., WINTER, G. (1993). Retroviral vectors displaying functional antibody fragments. Nucleic Acid Res. 21: 1081–1985

SCHNIERLE, B. S., STITZ, J., BOSCH, V., NOCKEN, F., MERGET-MILLITZER, H., ENGELSTADTER, M., KURTH, R., GRONER, B., CICHUTEK, K. (1997). Pseudotyping of murine leukemia virus with the envelope glycoproteins of HIV generates a retroviral vector with specificity of infection for CD4-expressing cells. Proc Natl Acad Sci USA 94(16):86408645.

SMITH C., LEE S. W., WONG E., GALLARDO H., PAGE K., GASPAR O., LEBOWSKI J., GILBOA E. (1996). Transient protection of human T-cells from human immunodeficiency virus type 1 infection by transduction with adeno-associated viral vectors which express RNA decoys. Antiviral Res. 32: 99–115

WATANABE, S. AND TEMIN, R M. (1983). Construction of a helper cell line for avian reticuloendotheliosis virus cloning vectors. Mol. Cell Biol. 3: 2241–2249

WEISS, R. (1993). Cellular receptors and viral glycoproteins involved in retroviral entry. In J. A. Levy (ed.). The Retroviridae 2: 1–108

WHITLOW, M. AND FILPULA, D., (1991). Single-Chain Fv proteins and their fusion proteins. Methods: A companion to Methods Enzymol. 2:97–105

YU, J. S., BURWICK, J. A, DRANOFF, G., BREAKEFIELD, X., (1997). Gene Therapy for metastatic Brain Tumors by Vaccination with Granulocyte-Macrophage-Colony-Stimulation Factor-Transduced Tumor Cells. H Gene Therapy 8:1065–1072

All references cited herein are incorporated by reference in their entirety.

SEQUENCE LISTING

```
<160> NUMBER OF SEQ ID NOS: 10

<210> SEQ ID NO 1
<211> LENGTH: 1030
<212> TYPE: DNA
<213> ORGANISM: Artificial Sequence
<220> FEATURE:
```

<223> OTHER INFORMATION: scFv encoding sequence
<220> FEATURE:
<221> NAME/KEY: CDS
<222> LOCATION: (44)...(1030)

<400> SEQUENCE: 1

```
tccaccactc tcgactcaag aaagctcctg acaaccaaga aga atg gac tgt ctc          55
                                             Met Asp Cys Leu
                                               1 acc aac ctc cga tcc gct gag ggt aaa gtt gac cag gcg agc aaa atc         103
Thr Asn Leu Arg Ser Ala Glu Gly Lys Val Asp Gln Ala Ser Lys Ile
  5              10                  15                  20 cta att ctc ctt gtg gct tgg tgg ggg ttt ggg acc act gcc gaa gtt         151
Leu Ile Leu Leu Val Ala Trp Trp Gly Phe Gly Thr Thr Ala Glu Val
                25                  30                  35 tcg act gcc cga gcg gcc cag ccg gcc atg gcc gag gtc aag ctg cag         199
Ser Thr Ala Arg Ala Ala Gln Pro Ala Met Ala Glu Val Lys Leu Gln
            40                  45                  50 cag tca ggg gct gag ctg gtg agg cct ggg gtc tca gtg aag att tcc         247
Gln Ser Gly Ala Glu Leu Val Arg Pro Gly Val Ser Val Lys Ile Ser
        55                  60                  65 tgc aag ggt tct ggc tac aca ttc act gat tat ggt atg agc tgg gtg         295
Cys Lys Gly Ser Gly Tyr Thr Phe Thr Asp Tyr Gly Met Ser Trp Val
 70                  75                  80 aaa cag agt cat gca aag agt cta gag tgg att gga ctt att agt act         343
Lys Gln Ser His Ala Lys Ser Leu Glu Trp Ile Gly Leu Ile Ser Thr
 85                  90                  95                 100 tac tat ggt gat cct agt tac aac cag agg ttc aag ggc aag gcc aca         391
Tyr Tyr Gly Asp Pro Ser Tyr Asn Gln Arg Phe Lys Gly Lys Ala Thr
                105                 110                 115 atg act gta gac aaa tcc tcc aac aca gcc tat ttg gaa ctt gcc aga         439
Met Thr Val Asp Lys Ser Ser Asn Thr Ala Tyr Leu Glu Leu Ala Arg
            120                 125                 130 ctg aca tct gag gat tct gcc att tat tat tgt gca aga tcg gat ggt         487
Leu Thr Ser Glu Asp Ser Ala Ile Tyr Tyr Cys Ala Arg Ser Asp Gly
        135                 140                 145 aat tac ggg tat tac tat gct ttg gac tac tgg ggc caa ggc act acg         535
Asn Tyr Gly Tyr Tyr Tyr Ala Leu Asp Tyr Trp Gly Gln Gly Thr Thr
    150                 155                 160 gtc acc gtc tcc tca ggt gga ggc ggt tca ggc gga ggt ggc tct ggc         583
Val Thr Val Ser Ser Gly Gly Gly Gly Ser Gly Gly Gly Gly Ser Gly
165                 170                 175                 180 ggt ggc gga tcg gat atc gag ctc act cag tct cca tct tct ttg gct         631
Gly Gly Gly Ser Asp Ile Glu Leu Thr Gln Ser Pro Ser Ser Leu Ala
                185                 190                 195 gtg tct cta ggg cag agg gcc acc ata tcc tgc aga gcc agt gaa agt         679
Val Ser Leu Gly Gln Arg Ala Thr Ile Ser Cys Arg Ala Ser Glu Ser
            200                 205                 210 gtt gat agt tat ggc gat agt ttt atg cac tgg tat cag cag aaa cca         727
Val Asp Ser Tyr Gly Asp Ser Phe Met His Trp Tyr Gln Gln Lys Pro
        215                 220                 225 gga cag cca ccc aaa ctc ctc atc tat cgt gca tcc aac cta gaa tct         775
Gly Gln Pro Pro Lys Leu Leu Ile Tyr Arg Ala Ser Asn Leu Glu Ser
    230                 235                 240 gga gtc cct gcc agg ttc agt ggc agt ggg tct gag tca gac ttc act         823
Gly Val Pro Ala Arg Phe Ser Gly Ser Gly Ser Glu Ser Asp Phe Thr
245                 250                 255                 260 ctc acc atc gat cct gtg gag gaa gat gat gct gca gtg tat tac tgt         871
Leu Thr Ile Asp Pro Val Glu Glu Asp Asp Ala Ala Val Tyr Tyr Cys
                265                 270                 275
```

-continued

| | |
|---|---|
| ctg caa agt atg gaa gat ccg tac acg ttc gga ggg ggg acc aag ctg<br>Leu Gln Ser Met Glu Asp Pro Tyr Thr Phe Gly Gly Gly Thr Lys Leu<br>            280                     285                      290 | 919 |
| gaa ata aaa cgg gcg gcc gca tcg ggc tcc ggg ggc ggt ggt tct ggt<br>Glu Ile Lys Arg Ala Ala Ala Ser Gly Ser Gly Gly Gly Gly Ser Gly<br>         295                      300                    305 | 967 |
| ggt ggt tct ggt ggt ggt ggt tct ggt ggt ggt ggt tct ggc gcc agc<br>Gly Gly Ser Gly Gly Gly Gly Ser Gly Gly Gly Gly Ser Gly Ala Ser<br>310                    315                   320 | 1015 |
| cca gtc cag ttt atc<br>Pro Val Gln Phe Ile<br>325 | 1030 |

<210> SEQ ID NO 2
<211> LENGTH: 927
<212> TYPE: DNA
<213> ORGANISM: Artificial Sequence
<220> FEATURE:
<223> OTHER INFORMATION: scFv encoding sequence
<220> FEATURE:
<221> NAME/KEY: CDS
<222> LOCATION: (1)...(927)

<400> SEQUENCE: 2

| | |
|---|---|
| atg gac tgt ctc acc aac ctc cga tcc gct gag ggt aaa gtt gac cag<br>Met Asp Cys Leu Thr Asn Leu Arg Ser Ala Glu Gly Lys Val Asp Gln<br>1                 5                    10                  15 | 48 |
| gcg agc aaa atc cta att ctc ctt gtg gct tgg tgg ggg ttt ggg acc<br>Ala Ser Lys Ile Leu Ile Leu Leu Val Ala Trp Trp Gly Phe Gly Thr<br>              20                      25                    30 | 96 |
| act gcc gaa gtt tcg act gcc cga gcg gcc cag ccg gcc atg gcc gag<br>Thr Ala Glu Val Ser Thr Ala Arg Ala Ala Gln Pro Ala Met Ala Glu<br>         35                      40                    45 | 144 |
| gtc aag ctg cag gag tca ggg act gaa ctt gtg aag cct ggg gct tca<br>Val Lys Leu Gln Glu Ser Gly Thr Glu Leu Val Lys Pro Gly Ala Ser<br>         50                      55                    60 | 192 |
| gtg aat ctg tct tgc aag gct tct ggc tac acc ttc acc agc tac tgg<br>Val Asn Leu Ser Cys Lys Ala Ser Gly Tyr Thr Phe Thr Ser Tyr Trp<br>65                70                    75                    80 | 240 |
| atg cac tgg ttg aag cag agg cct gga caa ggc ctt gag tgg atc gga<br>Met His Trp Leu Lys Gln Arg Pro Gly Gln Gly Leu Glu Trp Ile Gly<br>              85                      90                    95 | 288 |
| gag att gat cct gtt gat agt tat act aac tac aat caa aac ttc aag<br>Glu Ile Asp Pro Val Asp Ser Tyr Thr Asn Tyr Asn Gln Asn Phe Lys<br>                 100                 105               110 | 336 |
| ggc aag gcc aca ctg act gta gac aag tcc tcc acc aca gtc tac atg<br>Gly Lys Ala Thr Leu Thr Val Asp Lys Ser Ser Thr Thr Val Tyr Met<br>         115                      120                    125 | 384 |
| cac ctc agc agc ctg aca tct gag gac tct gcg gtc tat tac tgt gca<br>His Leu Ser Ser Leu Thr Ser Glu Asp Ser Ala Val Tyr Tyr Cys Ala<br>         130                      135                    140 | 432 |
| aga aag ggc tat gct atg gac tac tgg ggc caa ggg acc aac gtc acc<br>Arg Lys Gly Tyr Ala Met Asp Tyr Trp Gly Gln Gly Thr Asn Val Thr<br>145                150                    155                  160 | 480 |
| gtc tcc tca ggt gga tgc ggt tca ggc gga ggt ggc tct ggc ggt ggc<br>Val Ser Ser Gly Gly Cys Gly Ser Gly Gly Gly Gly Ser Gly Gly Gly<br>                 165                 170               175 | 528 |
| gga tcg gac atc gag ctc act cag tca cca gca atc atg tct gca tct<br>Gly Ser Asp Ile Glu Leu Thr Gln Ser Pro Ala Ile Met Ser Ala Ser<br>         180                      185                    190 | 576 |
| cca ggg gag aag gtc acc atg acc tgc agt gcc agc tca agt ata agt<br>Pro Gly Glu Lys Val Thr Met Thr Cys Ser Ala Ser Ser Ser Ile Ser | 624 |

-continued

```
                195                 200                 205
tac atg cac tgg tac cag cag aag cca ggc acc tcc ccc aaa aga tgg    672
Tyr Met His Trp Tyr Gln Gln Lys Pro Gly Thr Ser Pro Lys Arg Trp
    210                 215                 220 att tat gac aca tcc aaa ctg gct tct gga gtc cct gct cgc ttc agt    720
Ile Tyr Asp Thr Ser Lys Leu Ala Ser Gly Val Pro Ala Arg Phe Ser
225                 230                 235                 240 ggc agt ggg tct ggg acc tct tat tct ctc cca atc agc agc atg gag    768
Gly Ser Gly Ser Gly Thr Ser Tyr Ser Leu Pro Ile Ser Ser Met Glu
                245                 250                 255 gct gaa gat gct gcc act tat tac tgc cat cag cgg agt agt tac cca    816
Ala Glu Asp Ala Ala Thr Tyr Tyr Cys His Gln Arg Ser Ser Tyr Pro
            260                 265                 270 tgg acg ttc ggt gga ggg acc aag ctg gaa ata aaa cgg gcg gcc gca    864
Trp Thr Phe Gly Gly Gly Thr Lys Leu Glu Ile Lys Arg Ala Ala Ala
        275                 280                 285 tcg ggc tcc ggg ggc ggt ggt tct ggt ggt ggt tct ggt ggt ggt ggt    912
Ser Gly Ser Gly Gly Gly Gly Ser Gly Gly Gly Ser Gly Gly Gly Gly
    290                 295                 300 tct ggt ggt ggt ggt                                                927
Ser Gly Gly Gly Gly
305

<210> SEQ ID NO 3
<211> LENGTH: 990
<212> TYPE: DNA
<213> ORGANISM: Artificial Sequence
<220> FEATURE:
<223> OTHER INFORMATION: scFv encoding sequence
<220> FEATURE:
<221> NAME/KEY: CDS
<222> LOCATION: (1)...(990)

<400> SEQUENCE: 3 atg gac tgt ctc acc aac ctc cga tcc gct gag ggt aaa gtt gac cag     48
Met Asp Cys Leu Thr Asn Leu Arg Ser Ala Glu Gly Lys Val Asp Gln
1               5                   10                  15 gcg agc aaa atc cta att ctc ctt gtg gct tgg tgg ggg ttt ggg acc     96
Ala Ser Lys Ile Leu Ile Leu Leu Val Ala Trp Trp Gly Phe Gly Thr
                20                  25                  30 act gcc gaa gtt tcg act gcc cga gcg gcc cag ccg gcc atg gcc cag    144
Thr Ala Glu Val Ser Thr Ala Arg Ala Ala Gln Pro Ala Met Ala Gln
            35                  40                  45 gtg cag ctg cag cag tct ggg act gaa ctg gca aca cct ggg gcc tca    192
Val Gln Leu Gln Gln Ser Gly Thr Glu Leu Ala Thr Pro Gly Ala Ser
        50                  55                  60 gtg agg atg tcc tgc aag gct tct ggc tac gcc ttt act acc tac tgg    240
Val Arg Met Ser Cys Lys Ala Ser Gly Tyr Ala Phe Thr Thr Tyr Trp
65                  70                  75                  80 atg cac tgg gta aaa cag agg cct gga cag ggt ctg gaa tgg att gga    288
Met His Trp Val Lys Gln Arg Pro Gly Gln Gly Leu Glu Trp Ile Gly
                85                  90                  95 tac att aat cct acc act gat tat act gac tac aat ctg aag ttc aag    336
Tyr Ile Asn Pro Thr Thr Asp Tyr Thr Asp Tyr Asn Leu Lys Phe Lys
                100                 105                 110 gac aag gcc aca ttg act gca gac aaa tcc tcc agt aca gcc tac atg    384
Asp Lys Ala Thr Leu Thr Ala Asp Lys Ser Ser Ser Thr Ala Tyr Met
            115                 120                 125 caa ctg agc agc ctg aca tct gag gac tct gca gtc tat tac tgt gca    432
Gln Leu Ser Ser Leu Thr Ser Glu Asp Ser Ala Val Tyr Tyr Cys Ala
        130                 135                 140
```

```
aga tcg ggg tgg tcc tat gct atg gac tac tgg ggg caa ggg acc acg          480
Arg Ser Gly Trp Ser Tyr Ala Met Asp Tyr Trp Gly Gln Gly Thr Thr
145                 150                 155                 160 gtc acc atc tcc tca ggt gga ggc ggt tca ggc gga ggt ggc tct ggc          528
Val Thr Ile Ser Ser Gly Gly Gly Gly Ser Gly Gly Gly Gly Ser Gly
            165                 170                 175 ggt ggc gga tcg gac atc gag ctc act cag tct cca gca atc atg tct          576
Gly Gly Gly Ser Asp Ile Glu Leu Thr Gln Ser Pro Ala Ile Met Ser
        180                 185                 190 gca tct cca ggg gag aag gtc acc ata acc tgc agt gcc agc tca agt          624
Ala Ser Pro Gly Glu Lys Val Thr Ile Thr Cys Ser Ala Ser Ser Ser
    195                 200                 205 gta agt tac atg cac tgg ttc cag cag aag cca ggc act tct ccc aaa          672
Val Ser Tyr Met His Trp Phe Gln Gln Lys Pro Gly Thr Ser Pro Lys
210                 215                 220 ctc tgg att tat agc aca tcc aac ctg gct tct gga gtc cct gct cgc          720
Leu Trp Ile Tyr Ser Thr Ser Asn Leu Ala Ser Gly Val Pro Ala Arg
225                 230                 235                 240 ttc agt ggc agt gga tct ggg acc tct tac tct ctc aca atc agc cga          768
Phe Ser Gly Ser Gly Ser Gly Thr Ser Tyr Ser Leu Thr Ile Ser Arg
            245                 250                 255 atg gag gct gaa gat gct gcc act tat tac tgc cag caa agg agt agt          816
Met Glu Ala Glu Asp Ala Ala Thr Tyr Tyr Cys Gln Gln Arg Ser Ser
        260                 265                 270 tac cca ttc acg ttc ggc tcg ggc acc aag ctg gaa atc aaa cgg gcg          864
Tyr Pro Phe Thr Phe Gly Ser Gly Thr Lys Leu Glu Ile Lys Arg Ala
    275                 280                 285 gcc gca tcg ggc tcc ggg ggc ggt ggt tct ggt ggt ggt ggt tct ggt          912
Ala Ala Ser Gly Ser Gly Gly Gly Gly Ser Gly Gly Gly Gly Ser Gly
290                 295                 300 ggt ggt ggt tct ggt ggt ggt ggt tct ggc gcc agc cca gtc cag ttt          960
Gly Gly Gly Ser Gly Gly Gly Gly Ser Gly Ala Ser Pro Val Gln Phe
305                 310                 315                 320 atc ccc ctg ctt gtg ggt cta ggg att tca                                  990
Ile Pro Leu Leu Val Gly Leu Gly Ile Ser
            325                 330

<210> SEQ ID NO 4
<211> LENGTH: 946
<212> TYPE: DNA
<213> ORGANISM: Artificial Sequence
<220> FEATURE:
<223> OTHER INFORMATION: scFv encoding sequence
<220> FEATURE:
<221> NAME/KEY: CDS
<222> LOCATION: (1)...(945)

<400> SEQUENCE: 4 atg gac tgt ctc acc aac ctc cga tcc gct gag ggt aaa gtt gac cag           48
Met Asp Cys Leu Thr Asn Leu Arg Ser Ala Glu Gly Lys Val Asp Gln
1               5                   10                  15 gcg agc aaa atc cta att ctc ctt gtg gct tgg tgg ggg ttt ggg acc           96
Ala Ser Lys Ile Leu Ile Leu Leu Val Ala Trp Trp Gly Phe Gly Thr
                20                  25                  30 act gcc gaa gtt tcg act gcc cga gcg gcc cag ccg gcc atg gcc gag          144
Thr Ala Glu Val Ser Thr Ala Arg Ala Ala Gln Pro Ala Met Ala Glu
            35                  40                  45 gtc aag ctg cag cag tca ggg gct gag ctg gtg agg cct gga gct tca          192
Val Lys Leu Gln Gln Ser Gly Ala Glu Leu Val Arg Pro Gly Ala Ser
        50                  55                  60 gtg aag ctg tcc tgc aag act tct ggc ttc tcc ttc acc agc tac tgg          240
Val Lys Leu Ser Cys Lys Thr Ser Gly Phe Ser Phe Thr Ser Tyr Trp
```

```
atg aac tgg gtg aag ctg agg cct gga caa ggc ctt gag tgg att ggc      288
Met Asn Trp Val Lys Leu Arg Pro Gly Gln Gly Leu Glu Trp Ile Gly
             85                   90                   95 atg att cat cct tcc gat agt gaa act agt tta act cag agg ttc aag      336
Met Ile His Pro Ser Asp Ser Glu Thr Ser Leu Thr Gln Arg Phe Lys
            100                  105                  110 gac aag gcc aca ctg act gta gac aaa tcc tcc agc aca gcc tac atg      384
Asp Lys Ala Thr Leu Thr Val Asp Lys Ser Ser Ser Thr Ala Tyr Met
        115                  120                  125 caa ctc agc agc ccg aca tct gag gac tct gcg gtc tat tac tgt gca      432
Gln Leu Ser Ser Pro Thr Ser Glu Asp Ser Ala Val Tyr Tyr Cys Ala
        130                  135                  140 aga tct ctt tat gct aac tac ccc tcc tgg ttt act tac tgg ggc caa      480
Arg Ser Leu Tyr Ala Asn Tyr Pro Ser Trp Phe Thr Tyr Trp Gly Gln
145                  150                  155                  160 ggc acc acg gtc acc gtc tcc tca ggt gga ggc ggt tca ggc gga ggt      528
Gly Thr Thr Val Thr Val Ser Ser Gly Gly Gly Gly Ser Gly Gly Gly
                165                  170                  175 ggc tct ggc ggt ggc gga tcg gac atc gag ctc act cag tct cca acc      576
Gly Ser Gly Gly Gly Gly Ser Asp Ile Glu Leu Thr Gln Ser Pro Thr
            180                  185                  190 acc atg gct gca tct ccc ggg gag aag atc act atc acc tgc agt gcc      624
Thr Met Ala Ala Ser Pro Gly Glu Lys Ile Thr Ile Thr Cys Ser Ala
        195                  200                  205 agc tca agt ata agt tcc aat tac ttg cat tgg tat cag cag aag cca      672
Ser Ser Ser Ile Ser Ser Asn Tyr Leu His Trp Tyr Gln Gln Lys Pro
        210                  215                  220 gga ttc tcc cct aaa ctc ttg att tat agg aca tcc aat ctg gct tct      720
Gly Phe Ser Pro Lys Leu Leu Ile Tyr Arg Thr Ser Asn Leu Ala Ser
225                  230                  235                  240 gga gtc cca gct cgc ttc agt ggc agt ggg tct ggg acc tct tac tct      768
Gly Val Pro Ala Arg Phe Ser Gly Ser Gly Ser Gly Thr Ser Tyr Ser
                245                  250                  255 ctc aca att ggc acc atg gag gct gaa gat gtt gcc act tac tac tgc      816
Leu Thr Ile Gly Thr Met Glu Ala Glu Asp Val Ala Thr Tyr Tyr Cys
            260                  265                  270 cag cag ggt agt agt ata ccg tac acg ttc gga ggg ggg acc aag ctg      864
Gln Gln Gly Ser Ser Ile Pro Tyr Thr Phe Gly Gly Gly Thr Lys Leu
        275                  280                  285 gaa ata aaa cgg gcg gcc gca tcg ggc tcc ggg ggc ggt ggt tct ggt      912
Glu Ile Lys Arg Ala Ala Ala Ser Gly Ser Gly Gly Gly Gly Ser Gly
        290                  295                  300 ggt ggt ggt tct ggt ggt ggt ggt tct ggt ggt g                        946
Gly Gly Gly Ser Gly Gly Gly Gly Ser Gly Gly
305                  310                  315

<210> SEQ ID NO 5
<211> LENGTH: 906
<212> TYPE: DNA
<213> ORGANISM: Artificial Sequence
<220> FEATURE:
<223> OTHER INFORMATION: scFv encoding sequence
<220> FEATURE:
<221> NAME/KEY: CDS
<222> LOCATION: (1)...(906)

<400> SEQUENCE: 5 atg gac tgt ctc acc aac ctc cga tcc gct gag ggt aaa gtt gac cag       48
Met Asp Cys Leu Thr Asn Leu Arg Ser Ala Glu Gly Lys Val Asp Gln
  1               5                  10                  15
```

```
gcg agc aaa atc cta att ctc ctt gtg gct tgg tgg ggg ttt ggg acc      96
Ala Ser Lys Ile Leu Ile Leu Leu Val Ala Trp Trp Gly Phe Gly Thr
            20                  25                  30 act gcc gaa gtt tcg act gcc cga gcg gcc cag ccg gcc atg gcc cag     144
Thr Ala Glu Val Ser Thr Ala Arg Ala Ala Gln Pro Ala Met Ala Gln
        35                  40                  45 gta cag ctg cag cag tca gga gca gaa atg aaa aag ccc ggg gag tct     192
Val Gln Leu Gln Gln Ser Gly Ala Glu Met Lys Lys Pro Gly Glu Ser
50                  55                  60 ctg aaa atc tcc tgt aag ggt ttt gga tac gac ttt agc acc tac tgg     240
Leu Lys Ile Ser Cys Lys Gly Phe Gly Tyr Asp Phe Ser Thr Tyr Trp
65                  70                  75                  80 atc gcc tgg gtg cgc cag atg ccc ggg aaa ggc ctg gag tac atg ggg     288
Ile Ala Trp Val Arg Gln Met Pro Gly Lys Gly Leu Glu Tyr Met Gly
                85                  90                  95 ctc atc tat cct ggt gac tct gac acc aaa tac agc ccg tcc ttc caa     336
Leu Ile Tyr Pro Gly Asp Ser Asp Thr Lys Tyr Ser Pro Ser Phe Gln
            100                 105                 110 ggc cag gtc acc atc tca gcc gac aag tcc atc agc acc gcc tac ctg     384
Gly Gln Val Thr Ile Ser Ala Asp Lys Ser Ile Ser Thr Ala Tyr Leu
        115                 120                 125 cag tgg agc agc ctg aag gcc tcg gac acc gcc atg tat tac tgt gcg     432
Gln Trp Ser Ser Leu Lys Ala Ser Asp Thr Ala Met Tyr Tyr Cys Ala
    130                 135                 140 aga gtc tct gga tat tgt agt agt acc agc tgc tat gac tac tac tac     480
Arg Val Ser Gly Tyr Cys Ser Ser Thr Ser Cys Tyr Asp Tyr Tyr Tyr
145                 150                 155                 160 tac tac atg gac gtc tgg ggc cgg gga acc ctg gtc acc gtc tcg aga     528
Tyr Tyr Met Asp Val Trp Gly Arg Gly Thr Leu Val Thr Val Ser Arg
                165                 170                 175 ggt gga ggc ggt tca ggc gga ggt ggc tct ggc ggt ggc gga tcg gac     576
Gly Gly Gly Gly Ser Gly Gly Gly Gly Ser Gly Gly Gly Gly Ser Asp
            180                 185                 190 atc gtg atg acc cag tct cct tcc acc ctg tct gca tct gta gga gac     624
Ile Val Met Thr Gln Ser Pro Ser Thr Leu Ser Ala Ser Val Gly Asp
        195                 200                 205 aga gtc acc atg act tgc cgg gcc agt cag aac att aat atc tgg ttg     672
Arg Val Thr Met Thr Cys Arg Ala Ser Gln Asn Ile Asn Ile Trp Leu
    210                 215                 220 gcc tgg tat cag cag aaa cca ggg aaa gcc cct aag ctc ctg atc tat     720
Ala Trp Tyr Gln Gln Lys Pro Gly Lys Ala Pro Lys Leu Leu Ile Tyr
225                 230                 235                 240 aag gcg tcc act tta gag agt ggg gtc ccg tca agg ttc agc ggc agt     768
Lys Ala Ser Thr Leu Glu Ser Gly Val Pro Ser Arg Phe Ser Gly Ser
                245                 250                 255 gga tct ggg aca gaa ttc act ctc acc atc agc ggc ctg cag cct gat     816
Gly Ser Gly Thr Glu Phe Thr Leu Thr Ile Ser Gly Leu Gln Pro Asp
            260                 265                 270 gat ttt gca agt tat tac tgt caa cgg tat gat agt gac tgg tcg ttc     864
Asp Phe Ala Ser Tyr Tyr Cys Gln Arg Tyr Asp Ser Asp Trp Ser Phe
        275                 280                 285 ggc caa ggg acc aag ctg gag atc aaa cgt gcg gcc gca tcg             906
Gly Gln Gly Thr Lys Leu Glu Ile Lys Arg Ala Ala Ala Ser
    290                 295                 300
```

<210> SEQ ID NO 6
<211> LENGTH: 329
<212> TYPE: PRT
<213> ORGANISM: Artificial Sequence
<220> FEATURE:
<223> OTHER INFORMATION: scFv

<400> SEQUENCE: 6

```
Met Asp Cys Leu Thr Asn Leu Arg Ser Ala Glu Gly Lys Val Asp Gln
 1               5                  10                  15
Ala Ser Lys Ile Leu Ile Leu Val Ala Trp Trp Gly Phe Gly Thr
            20                  25                  30
Thr Ala Glu Val Ser Thr Ala Arg Ala Ala Gln Pro Ala Met Ala Glu
         35                  40                  45
Val Lys Leu Gln Gln Ser Gly Ala Glu Leu Val Arg Pro Gly Val Ser
     50                  55                  60
Val Lys Ile Ser Cys Lys Gly Ser Gly Tyr Thr Phe Thr Asp Tyr Gly
 65                  70                  75                  80
Met Ser Trp Val Lys Gln Ser His Ala Lys Ser Leu Glu Trp Ile Gly
                 85                  90                  95
Leu Ile Ser Thr Tyr Tyr Gly Asp Pro Ser Tyr Asn Gln Arg Phe Lys
            100                 105                 110
Gly Lys Ala Thr Met Thr Val Asp Lys Ser Ser Asn Thr Ala Tyr Leu
        115                 120                 125
Glu Leu Ala Arg Leu Thr Ser Glu Asp Ser Ala Ile Tyr Tyr Cys Ala
    130                 135                 140
Arg Ser Asp Gly Asn Tyr Gly Tyr Tyr Ala Leu Asp Tyr Trp Gly
145                 150                 155                 160
Gln Gly Thr Thr Val Thr Val Ser Ser Gly Gly Gly Ser Gly Gly
                165                 170                 175
Gly Gly Ser Gly Gly Gly Ser Asp Ile Glu Leu Thr Gln Ser Pro
            180                 185                 190
Ser Ser Leu Ala Val Ser Leu Gly Gln Arg Ala Thr Ile Ser Cys Arg
        195                 200                 205
Ala Ser Glu Ser Val Asp Ser Tyr Gly Asp Ser Phe Met His Trp Tyr
    210                 215                 220
Gln Gln Lys Pro Gly Gln Pro Pro Lys Leu Leu Ile Tyr Arg Ala Ser
225                 230                 235                 240
Asn Leu Glu Ser Gly Val Pro Ala Arg Phe Ser Gly Ser Gly Ser Glu
                245                 250                 255
Ser Asp Phe Thr Leu Thr Ile Asp Pro Val Glu Glu Asp Ala Ala
            260                 265                 270
Val Tyr Tyr Cys Leu Gln Ser Met Glu Asp Pro Tyr Thr Phe Gly Gly
        275                 280                 285
Gly Thr Lys Leu Glu Ile Lys Arg Ala Ala Ala Ser Gly Ser Gly Gly
    290                 295                 300
Gly Gly Ser Gly Gly Gly Ser Gly Gly Gly Ser Gly Gly Gly Gly
305                 310                 315                 320
Ser Gly Ala Ser Pro Val Gln Phe Ile
                325
```

<210> SEQ ID NO 7
<211> LENGTH: 309
<212> TYPE: PRT
<213> ORGANISM: Artificial Sequence
<220> FEATURE:
<223> OTHER INFORMATION: scFv

<400> SEQUENCE: 7

```
Met Asp Cys Leu Thr Asn Leu Arg Ser Ala Glu Gly Lys Val Asp Gln
 1               5                  10                  15
```

```
Ala Ser Lys Ile Leu Ile Leu Leu Val Ala Trp Trp Gly Phe Gly Thr
            20                  25                  30

Thr Ala Glu Val Ser Thr Ala Arg Ala Ala Gln Pro Ala Met Ala Glu
        35                  40                  45

Val Lys Leu Gln Glu Ser Gly Thr Glu Leu Val Lys Pro Gly Ala Ser
    50                  55                  60

Val Asn Leu Ser Cys Lys Ala Ser Gly Tyr Thr Phe Thr Ser Tyr Trp
65                  70                  75                  80

Met His Trp Leu Lys Gln Arg Pro Gly Gln Gly Leu Glu Trp Ile Gly
                85                  90                  95

Glu Ile Asp Pro Val Asp Ser Tyr Thr Asn Tyr Asn Gln Asn Phe Lys
            100                 105                 110

Gly Lys Ala Thr Leu Thr Val Asp Lys Ser Ser Thr Thr Val Tyr Met
        115                 120                 125

His Leu Ser Ser Leu Thr Ser Glu Asp Ser Ala Val Tyr Tyr Cys Ala
130                 135                 140

Arg Lys Gly Tyr Ala Met Asp Tyr Trp Gly Gln Gly Thr Asn Val Thr
145                 150                 155                 160

Val Ser Ser Gly Gly Cys Gly Ser Gly Gly Gly Ser Gly Gly Gly Gly
                165                 170                 175

Gly Ser Asp Ile Glu Leu Thr Gln Ser Pro Ala Ile Met Ser Ala Ser
            180                 185                 190

Pro Gly Glu Lys Val Thr Met Thr Cys Ser Ala Ser Ser Ser Ile Ser
        195                 200                 205

Tyr Met His Trp Tyr Gln Gln Lys Pro Gly Thr Ser Pro Lys Arg Trp
    210                 215                 220

Ile Tyr Asp Thr Ser Lys Leu Ala Ser Gly Val Pro Ala Arg Phe Ser
225                 230                 235                 240

Gly Ser Gly Ser Gly Thr Ser Tyr Ser Leu Pro Ile Ser Ser Met Glu
                245                 250                 255

Ala Glu Asp Ala Ala Thr Tyr Tyr Cys His Gln Arg Ser Ser Tyr Pro
            260                 265                 270

Trp Thr Phe Gly Gly Gly Thr Lys Leu Glu Ile Lys Arg Ala Ala Ala
        275                 280                 285

Ser Gly Ser Gly Gly Gly Ser Gly Gly Gly Ser Gly Gly Gly Gly
    290                 295                 300

Ser Gly Gly Gly Gly
305

<210> SEQ ID NO 8
<211> LENGTH: 330
<212> TYPE: PRT
<213> ORGANISM: Artificial Sequence
<220> FEATURE:
<223> OTHER INFORMATION: scFv

<400> SEQUENCE: 8

Met Asp Cys Leu Thr Asn Leu Arg Ser Ala Glu Gly Lys Val Asp Gln
1               5                   10                  15

Ala Ser Lys Ile Leu Ile Leu Leu Val Ala Trp Trp Gly Phe Gly Thr
            20                  25                  30

Thr Ala Glu Val Ser Thr Ala Arg Ala Ala Gln Pro Ala Met Ala Gln
        35                  40                  45

Val Gln Leu Gln Gln Ser Gly Thr Glu Leu Ala Thr Pro Gly Ala Ser
    50                  55                  60
```

-continued

```
Val Arg Met Ser Cys Lys Ala Ser Gly Tyr Ala Phe Thr Thr Tyr Trp
 65                  70                  75                  80

Met His Trp Val Lys Gln Arg Pro Gly Gln Gly Leu Glu Trp Ile Gly
                 85                  90                  95

Tyr Ile Asn Pro Thr Thr Asp Tyr Thr Asp Tyr Asn Leu Lys Phe Lys
            100                 105                 110

Asp Lys Ala Thr Leu Thr Ala Asp Lys Ser Ser Thr Ala Tyr Met
        115                 120                 125

Gln Leu Ser Ser Leu Thr Ser Glu Asp Ser Ala Val Tyr Tyr Cys Ala
    130                 135                 140

Arg Ser Gly Trp Ser Tyr Ala Met Asp Tyr Trp Gly Gln Gly Thr Thr
145                 150                 155                 160

Val Thr Ile Ser Ser Gly Gly Gly Ser Gly Gly Gly Ser
                165                 170                 175

Gly Gly Gly Ser Asp Ile Glu Leu Thr Gln Ser Pro Ala Ile Met Ser
            180                 185                 190

Ala Ser Pro Gly Glu Lys Val Thr Ile Thr Cys Ser Ala Ser Ser Ser
        195                 200                 205

Val Ser Tyr Met His Trp Phe Gln Gln Lys Pro Gly Thr Ser Pro Lys
    210                 215                 220

Leu Trp Ile Tyr Ser Thr Ser Asn Leu Ala Ser Gly Val Pro Ala Arg
225                 230                 235                 240

Phe Ser Gly Ser Gly Ser Gly Thr Ser Tyr Ser Leu Thr Ile Ser Arg
                245                 250                 255

Met Glu Ala Glu Asp Ala Ala Thr Tyr Tyr Cys Gln Gln Arg Ser Ser
            260                 265                 270

Tyr Pro Phe Thr Phe Gly Ser Gly Thr Lys Leu Glu Ile Lys Arg Ala
        275                 280                 285

Ala Ala Ser Gly Ser Gly Gly Gly Ser Gly Gly Gly Ser Gly
    290                 295                 300

Gly Gly Ser Gly Gly Gly Ser Gly Ala Ser Pro Val Gln Phe
305                 310                 315                 320

Ile Pro Leu Leu Val Gly Leu Gly Ile Ser
                325                 330
```

<210> SEQ ID NO 9
<211> LENGTH: 315
<212> TYPE: PRT
<213> ORGANISM: Artificial Sequence
<220> FEATURE:
<223> OTHER INFORMATION: scFv

<400> SEQUENCE: 9

```
Met Asp Cys Leu Thr Asn Leu Arg Ser Ala Glu Gly Lys Val Asp Gln
 1               5                  10                  15

Ala Ser Lys Ile Leu Ile Leu Leu Val Ala Trp Trp Gly Phe Gly Thr
            20                  25                  30

Thr Ala Glu Val Ser Thr Ala Arg Ala Ala Gln Pro Ala Met Ala Glu
        35                  40                  45

Val Lys Leu Gln Gln Ser Gly Ala Glu Leu Val Arg Pro Gly Ala Ser
    50                  55                  60

Val Lys Leu Ser Cys Lys Thr Ser Gly Phe Ser Phe Thr Ser Tyr Trp
 65                  70                  75                  80

Met Asn Trp Val Lys Leu Arg Pro Gly Gln Gly Leu Glu Trp Ile Gly
                 85                  90                  95
```

-continued

```
Met Ile His Pro Ser Asp Ser Glu Thr Ser Leu Thr Gln Arg Phe Lys
                100                 105                 110

Asp Lys Ala Thr Leu Thr Val Asp Lys Ser Ser Thr Ala Tyr Met
            115                 120                 125

Gln Leu Ser Ser Pro Thr Ser Glu Asp Ser Ala Val Tyr Tyr Cys Ala
        130                 135                 140

Arg Ser Leu Tyr Ala Asn Tyr Pro Ser Trp Phe Thr Tyr Trp Gly Gln
145                 150                 155                 160

Gly Thr Thr Val Thr Val Ser Ser Gly Gly Gly Ser Gly Gly Gly
                165                 170                 175

Gly Ser Gly Gly Gly Ser Asp Ile Glu Leu Thr Gln Ser Pro Thr
            180                 185                 190

Thr Met Ala Ala Ser Pro Gly Glu Lys Ile Thr Ile Thr Cys Ser Ala
        195                 200                 205

Ser Ser Ser Ile Ser Ser Asn Tyr Leu His Trp Tyr Gln Gln Lys Pro
210                 215                 220

Gly Phe Ser Pro Lys Leu Leu Ile Tyr Arg Thr Ser Asn Leu Ala Ser
225                 230                 235                 240

Gly Val Pro Ala Arg Phe Ser Gly Ser Gly Ser Gly Thr Ser Tyr Ser
                245                 250                 255

Leu Thr Ile Gly Thr Met Glu Ala Glu Asp Val Ala Thr Tyr Tyr Cys
            260                 265                 270

Gln Gln Gly Ser Ser Ile Pro Tyr Thr Phe Gly Gly Thr Lys Leu
        275                 280                 285

Glu Ile Lys Arg Ala Ala Ala Ser Gly Ser Gly Gly Gly Ser Gly
290                 295                 300

Gly Gly Ser Gly Gly Gly Gly Ser Gly Gly
305                 310                 315

<210> SEQ ID NO 10
<211> LENGTH: 302
<212> TYPE: PRT
<213> ORGANISM: Artificial Sequence
<220> FEATURE:
<223> OTHER INFORMATION: scFv

<400> SEQUENCE: 10

Met Asp Cys Leu Thr Asn Leu Arg Ser Ala Glu Gly Lys Val Asp Gln
  1               5                  10                  15

Ala Ser Lys Ile Leu Ile Leu Leu Val Ala Trp Trp Phe Gly Thr
            20                  25                  30

Thr Ala Glu Val Ser Thr Ala Arg Ala Ala Gln Pro Ala Met Ala Gln
        35                  40                  45

Val Gln Leu Gln Gln Ser Gly Ala Glu Met Lys Lys Pro Gly Glu Ser
    50                  55                  60

Leu Lys Ile Ser Cys Lys Gly Phe Gly Tyr Asp Phe Ser Thr Tyr Trp
65                  70                  75                  80

Ile Ala Trp Val Arg Gln Met Pro Gly Lys Gly Leu Glu Tyr Met Gly
                85                  90                  95

Leu Ile Tyr Pro Gly Asp Ser Asp Thr Lys Tyr Ser Pro Ser Phe Gln
            100                 105                 110

Gly Gln Val Thr Ile Ser Ala Asp Lys Ser Ile Ser Thr Ala Tyr Leu
        115                 120                 125

Gln Trp Ser Ser Leu Lys Ala Ser Asp Thr Ala Met Tyr Tyr Cys Ala
    130                 135                 140
```

-continued

```
Arg Val Ser Gly Tyr Cys Ser Ser Thr Ser Cys Tyr Asp Tyr Tyr Tyr
145                 150                 155                 160

Tyr Tyr Met Asp Val Trp Gly Arg Gly Thr Leu Val Thr Val Ser Arg
            165                 170                 175

Gly Gly Gly Gly Ser Gly Gly Gly Ser Gly Gly Gly Gly Ser Asp
        180                 185                 190

Ile Val Met Thr Gln Ser Pro Ser Thr Leu Ser Ala Ser Val Gly Asp
        195                 200                 205

Arg Val Thr Met Thr Cys Arg Ala Ser Gln Asn Ile Asn Ile Trp Leu
        210                 215                 220

Ala Trp Tyr Gln Gln Lys Pro Gly Lys Ala Pro Lys Leu Leu Ile Tyr
225                 230                 235                 240

Lys Ala Ser Thr Leu Glu Ser Gly Val Pro Ser Arg Phe Ser Gly Ser
            245                 250                 255

Gly Ser Gly Thr Glu Phe Thr Leu Thr Ile Ser Gly Leu Gln Pro Asp
            260                 265                 270

Asp Phe Ala Ser Tyr Tyr Cys Gln Arg Tyr Asp Ser Asp Trp Ser Phe
        275                 280                 285

Gly Gln Gly Thr Lys Leu Glu Ile Lys Arg Ala Ala Ala Ser
290                 295                 300
```

The invention claimed is:

1. A cell targeting vector, comprising a DNA sequence encoding a single chain antibody fragment (scFv), characterized in that the single chain antibody fragment comprises amino acid residues 46–329 of SEQ ID NO:6.

2. The cell targeting vector according to claim 1, further comprising a DNA sequence encoding a spleen necrosis virus (SNV) env leader comprising amino acid residues 1–45 of SEQ ID NO:6.

3. The cell targeting vector of claim 1, wherein the vector is T cell specific.

4. A cell targeting vector comprising (a) a DNA sequence encoding a single chain antibody fragment (scFV) comprising amino acid residues 46–329 of SEQ ID NO:6 and (b) a therapeutic gene, wherein the vector is from SNV.

* * * * *